United States Patent [19]

Tsai et al.

[11] Patent Number: 4,673,707
[45] Date of Patent: Jun. 16, 1987

[54] SYNTHETIC POLYMERS WITH GLYCOSIDE SIDE CHAINS

[75] Inventors: John J. Tsai, Belle Mead; Martin M. Tessler, Edison, both of N.J.

[73] Assignee: National Starch and Chemical Corporation, Bridgewater, N.J.

[21] Appl. No.: 814,131

[22] Filed: Dec. 27, 1985

[51] Int. Cl.$^4$ ............................................ C07H 15/02
[52] U.S. Cl. .............................. 525/54.2; 525/54.21; 527/200; 527/207; 527/300; 527/313; 527/314; 530/360; 530/374; 536/56; 536/102
[58] Field of Search ................... 525/54.2, 54.21, 54.1; 530/360, 374; 527/200, 207, 300, 313, 314; 536/56, 102

[56] References Cited

U.S. PATENT DOCUMENTS

| | | | |
|---|---|---|---|
| 3,356,652 | 12/1967 | Ray-Chaudhuri | 527/300 |
| 3,931,148 | 1/1976 | Langdon | 536/18.3 |
| 4,077,894 | 3/1978 | Langdon et al. | 536/18.3 |
| 4,328,337 | 5/1982 | Kawasaki et al. | 536/119 |

FOREIGN PATENT DOCUMENTS 625644  7/1939  United Kingdom .

OTHER PUBLICATIONS

"The Direct Coupling of Oligosaccharides to Protein & Derivatized Gels", pp. 426–428; Archives of Biochemistry & Biophysics; 163; 1974.
"Enzyme Stabilization of Covalent Attachment of Carbohydrate"; pp. 777–779; Archives of Biochemistry & Biophysics; 167; 1975.
"Preparation and Nutritional Properties of Caseins Covalently Modified with Sugars. Reductive Alkylation of Lysines with Glucose, Fructose or Lactose", H. S. Lee et al.; pp. 1094–1098; J. Agric. Food Chem.; vol. 27, No. 5, 1979.
"Attachment of Thioglycosides to Proteins; Enhancement of Liver Membrane Binding", pp. 3963–3968; Krantz et al., Biochemistry, vol. 15, No. 18, 1976.
"In Vitro Digestibility and Functional Properties of Chemically Modified Casein"; L. C. Sen et al.; pp. 348–353; J. Argic. Food. Chem.; vol. 29, No. 2, 1981.

Primary Examiner—John Kight
Assistant Examiner—Nathan M. Nutter
Attorney, Agent, or Firm—Margaret B. Kelley; Edwin M. Szala

[57] ABSTRACT

Derivatized polymers containing glycoside side chains linked to the polymer by ether, sulfide, or amine linkages are prepared by reacting a polymer containing alcohol, thiol, and/or amine groups with a glycidyl glycoside having the formula

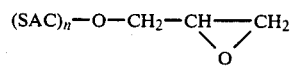

where $(SAC)_n$ represents a saccharide residue with n being 1–20. Typical polymers include poly(vinyl) alcohol, poly(ethyleneimine), poly(dimethylaminopropyl methacrylamide), and proteins such as caseinate or gluten. Typical glycosides are glycoside of glucose and maltodextrin-10.

21 Claims, No Drawings

SYNTHETIC POLYMERS WITH GLYCOSIDE SIDE CHAINS

BACKGROUND OF THE INVENTION

This invention relates to the polymers formed by the reaction of amine-containing and/or hydroxy-containing synthetic polymers with the halohydrin glycoside of monosaccharides or oligosaccharides.

Ethylenically unsaturated mono- and disaccharide glycoside derivatives as well as homo- and copolymers derived therefrom have been prepared. See, for example, U.S. Pat. No. 3,356,652 issued on Dec. 5, 1967 to D. Ray-Chaudhuri which describes the preparation of a glycoside containing an ethylenically unsaturated sidechain linked to the number 1 carbon of a 2,3,4,6-tetra-O-acetylglucose molecule. The homo- and copolymers prepared from the acetylated glycosidic monomers are soluble in organic solvents. They are prepared by reacting a tetraacetylglycosyl halide with a monohydroxy or monocarboxy ethylenically unsaturated monomer. Upon deacetylation, the homo- and copolymers having a mole fraction of at least about 20% of the glucoside derivatives become readily water soluble with a greater hydrophilic character than other commonly available synthetic water soluble polymers. The polymers contain monosaccharide side chains represented by the formula

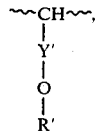

where R' represents a residue of a monosaccharide which is bonded at its 1-position and Y' is the residue after the polymerization of one of the following groups:

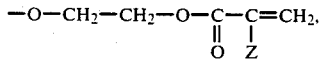

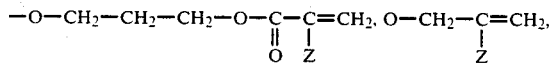

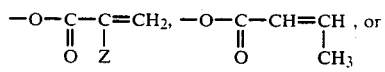

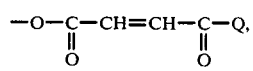

with Z being hydrogen or methyl and Q being a $C_1$-$C_4$ oxyalkyl group. The polymers are described as having broad utility in the adhesive, textile, and paper industries.

Similarly, U.S. Pat. No. 4,328,337 issued May 4, 1982 to T. Kawasaki et al. describes the preparation of polymers having repeating mono- or disaccharide side chains represented by the formula

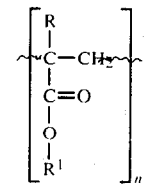

where R represents a hydrogen atom or a methyl group, $R^1$ represents a residue of a saccharide selected from the group consisting of glucose, fructose, maltose, mannose, lactose, and cellobiose, which is acyl-bonded at its 1-position, and n is 10-1000. They are prepared by homopolymerizing (meth)acryloyl mono- or disaccharide glycosides, e.g.,

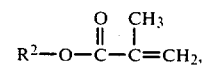

where $R^2$ represents an acetylated glucose residue acryl-bonded at its 1-position, and then de-acetylating the resulting polymer using an agent such as sodium methylate and ammonia at lower than room temperature. They may also be synthesized by bonding the saccharide chains to the main chain of the polymer, e.g., by reacting a polymer of acrylic or methacrylic acid with the compound obtained by orthoesterifying the hydroxyl group of the terminal reducing part of the acetylated saccharide and then de-acetylating the final polymer. The polymers are wter soluble with excellent bio-adaptability and membrane-forming properties. When cross-linked, the homopolymers have a high water-retaining property which is useful for many medical treatments.

In the prior art, the modifications of polyamines (e.g., proteins) with carbohydrates were made via reductive amination (e.g., using sodium cyanoborohydride), amide formation (e.g., using 2-imino-2-methoxyethyl-thioglycoside), or diazo coupling. The first two methods require the presence of primary or secondary amines. The reductive amination reaction results in an acyclic poly-alcohol attached to the nitrogen via a carbon-nitrogen bond. The thioglycoside, used in the amide formation or diazo coupling, is relatively stable to acid hydrolysis, i.e., cleavage of the glycoside bond. The reaction of reducing sugars with α-amino lysyl residues of casein in the presence of sodium cyanoborohydride is described in "Preparation and Nutritional Properties of Caseins Covalently Modified with Sugar. Reductive Alkylation of Lysines with Glucose, Fructose, or Lactose" by H. S. Lee et al., *J. Agric. Food Chem.* 27, #5, p. 1094 (1979). The covalent attachment of glycosides to proteins by amidination, diazo coupling reaction, and amide formation is described in "Attachment of Thioglycosides to Proteins: Enhancement of Liver Membrane Binding", by M. J. Krantz et al., *Biochemistry* 15, #18, p. 3963 (1976).

In U.S. Pat. No.3,931,148 issued on January 6, 1976 to W. Langdon, novel neutral and cationic glycosidic surfactants are prepared by reacting a 2-hydroxy-3-chloropropyl glycoside of a mono- or polysaccharide with an alkyl amine which contains at least one hydrophobic $C_8$-$C_{18}$ alkyl group. The alkyl amines are described as having 8-30 carbon atoms which may be primary, secondary, tertiary, aliphatic, saturated or unsaturated, alicyclic aralkyl. The glycosides are described as being useful in areas requiring surfactants exhibiting biodegradability, alkali solubility and stability.

It is the object of this invention to produce a novel class of monosaccharide and oligosaccharide derivatives of synthetic polymers and proteins.

SUMMARY

The present invention provides synthetic polymers represented by the general formula

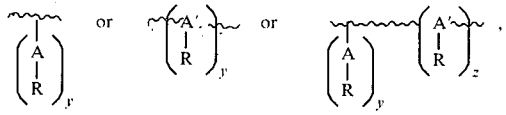

wherein A is O, S, $S^+R^1$, NH, $NR^1$, or $N^+(R^1)R^2X^-$; A' is S, N, $N^+HX^-$, or $N^+R^1X^-$; X is an anion, R is $-CH_2-CH(OH)-CH_2-O-(SAC)_n$; $R^1$ and $R^2$ are the same or different and selected from the group consisting of R and substituted or unsubstituted alkyl, cycloalkyl, aralkyl, and alkaryl groups; $(SAC)_n$ represents a saccharide residue with n being 1–20; y and z are at least one, with the proviso that when y and z are $>1$ the $-(A-R)_y$, $-(A'-R)_y$ and/or $-(A'-R)_z$ groups may be the same or different; represents a polymer chain; and wherein the R group contains an acetal or ketal linkage from the reducing end of $(SAC)_n$ to the 3-position of the 2-hydroxypropyl moiety (i.e., $-CH_2-CH-(OH)-CH_2-$) and an ether, sulfide, or amine linkage from the 1-position of the hydroxypropyl moiety to the O, S, or N group of the polymer. It should be noted that under acid conditions the NH or $NR^1$ group in the polymers may be protonated.

Suitable polymers contain alcohol groups such as

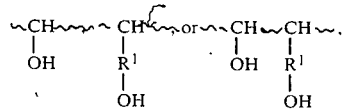

thiol groups such as

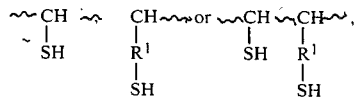

or amine groups such as

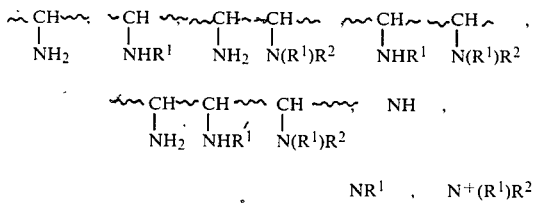

$NR^1$ , $N^+(R^1)R^2$ , or any combination containing pendant or chain-containing N groups.

The present invention permits the modification of polymers containing tertiary amines and/or other nucleophiles (e.g., thiol groups). The cyclic glycoside remains intact. The glycoside moiety can be easily remove, if desired, by acid hydrolysis. This is different from the irreversible modification provided by the prior art. The modification of polyamines (e.g., proteins) with carbohydrates were previously carried out by (1) reductive amination using sodium cyanoborohydride, (2) amide formation (e.g., with 2-imimo-2-methoxyethyl thioglycoside), or (3) diazo coupling. These processes result in products which cannot be reversed or which cannot be easily reversed by simple acid hydrolysis.

DETAILED DESCRIPTION OF THE PREFERRED EMBODIMENTS

Glycosides may be prepared from mono- and polysaccharides which contain a reducing carbon atom. This carbon atom, which is located in the terminal saccharide ring, is capable of reacting with alcohol to form glycosidic products attached by an acetal or ketal linkage, depending on the mono- or polysaccharide employed.

The glycosides which are applicable for use in the preparing the polymers include halohydrin or glycidyl glycosides having the general formula:

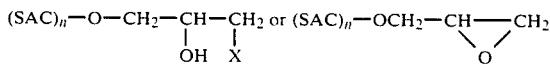

wherein $(SAC)_n-O-$ is as defined above. It represents a mono- or polysaccharide where O is attached to the reducing glycosidic carbon atom in the terminal saccharide ring of $(SAC)_n$, X is chlorine or bromine, and n is 1 to 20.

W. Langdon (discussed above) prepares similar glycosides by reacting monosaccharides and polysaccharides which are hydrolyzable to monosaccharides (including starch and cellulose) at temperatures of about 94° to 108° C. with 3-chloro-1,2-propandiol in the presence of about 0.01 to 2.0 weight percent, based on the reactants, of a strong acid catalyst. The procedure, when used with polysaccharides, produces severely hydrolyzed products. It also produces dark colored products, when used with monosaccharides and polysaccharides, probably due to charring caused by the acid at such high reaction temperatures.

In contrast to Langdon, the glycosides are preferably prepared by reacting a mono- or poly-saccharide in an excess of 3-halo-1,2-propandiol in the presence of a cation exchange resin. By employing a cation exchange resin, mono- and polysaccharide glycosides may be prepared at moderate temperatures without charring and with only minimal hydrolysis of the polysaccharide occurring. Additionally, no neutralization step is required as in acid-catalyzed systems as the catalyst may be easily removed by filtration.

The reaction is conducted with stirring at a temperature of about 55°–80° C., preferably 60°–65° C. over a period of about 3–20 hours, preferably 6–8 hours. By employing the preferred lower temperatures and shortened reaction times, the amount of oligosaccharide formation and polysaccharide degradation is reduced. After the reaction is complete, the mixture is filtered in order to remove the cation exchange resin. The excess diol may then be removed by a number of methods including, for example, vacuum distillation or washing with organic solvents in order to obtain the 3-halo-2-hydroxypropyl glycoside. When monosaccharide glycoside reagents are prepared, the diol may be removed from the glycoside by vacuum distillation, preferably at a temperature of about 80° C. and a pressure of 2 mm Hg. or lower temperatures and pressures. After distillation, the glycoside may optionally be washed with an organic solvent such as acetone or ethyl acetate. Glycosides prepared with polysaccharides may be purified by vacuum distillation, however, distillation temperatures above about 60° C. may cause some degradation. These glycosides are preferably recovered by suspending the glycoside/diol mixture in an organic solvent and filtering a number of times to remove the excess diol and other impurities.

The glycidyl glycosides useful herein may be prepared by reacting a 3-halo-2-hydroxypropyl glycoside with an alkali metal hydroxide in order to form the epoxide group. Typically, the glycoside is mixed with an aqueous alkaline solution while cooling. The mixture is neutralized with acid and then dissolved in alcohol in order to precipitate the metal salts formed. After filtration, the glycidyl glycoside may be recovered by removing the alcohol and water by vacuum distillation.

The monosaccharides which may be employed in the preparation of the glycoside reagent include glucose, fructose, sorbose, mannose, galactose, talose, allose, altrose, gulose, idose, arabinose, xylose, lyxose, ribose, and other similar monosaccharides. Oligosaccharides which may be employed in the preparation of the glycosides include maltose, gentiobiose, lactose, cellobiose, maltodextrins or starch having a dextrose equivalent (D.E.) of 5 or greater and other similar polysaccharides comprising no more than about 20 saccharide units. Any oligosaccharide or polysaccharide which can be hydrolyzed to produce a reducing end group is also suitable.

The halogenated propandiols which may be employed include 3-chloro-1,2-propandiol and 3-bromo-1,2-propandiol. The use of the chloro derivative is preferred due to its commercial availability and lower cost. The particular saccharide employed and its degree of solubility in the halogenated propandiol will determine the minimum amount of reagent required. While a saccharide to diol ratio of as little as 1:1.4 has been employed, a preferred ratio is at least 1:3 to 1:6, most preferably 1:5. As described above, monosaccharides and oligosaccharides of up to about 20 saccharide units which contain a reducing carbon atom are applicable herein. It was found that as the number of saccharide units increases the oligosaccharide becomes less reactive and more difficult to dissolve in the 3-halo-1,2-propandiol without employing undesirably high temperatures which cause significant degradation.

Any cation exchange resin may be used in the glycoside preparation. Suitable exchange resins include sulfonated-crosslinked polystyrene such as commercially available Amberlite IR-120 from Rohm and Haas, Dowex 50 from Dow Chemical and Permutit Q from Permutit; sulfonated phenolics such as Duolite C-3 from Diamond Shamrock; and sulfonated coals such as Zeo Karb H from Permutit. The preferred cation exchange resin is Dowex 50. The amount of resin useful herein is about 1 part resin to 2-8 parts by weight of saccharide, preferably 1 part resin to 4-5 parts saccharide.

Either the halohydrin or glycidyl glycoside reagent may be used in the preparation of the polymers herein as the glycosides will only react with the polymers under alkaline conditions after the halohydrin is first converted to the epoxide form.

Synthetic polymers suitable for reaction with the 3-chloro-2-hydroxypropyl glycosides herein include polymers or copolymers which are soluble or dispersible in water or highly polar solvents such as N-methylpyrrolidinone, dimethyl formamide, or dimethyl sulfoxide. Some homopolymers may be insoluble in water or polar solvents, but their copolymers with more hydrophilic monomers, which can increase their solubility, may be used. These may include, for example, poly(vinyl alcohols); poly(hydroxystyrenes) such as poly[4-(4-hydroxybutoxymethyl)styrene], poly[4-(2-hydroxyethoxymethyl)styrene], and poly(2-, 3-, or 4-hydroxymethylstyrene); poly(hydroxyalkyl acrylate or methacrylate) and poly(hydroxyalkyl acrylamide or methacrylamide); poly(alkylene sulfides) such as poly(ethylene sulfide) and poly(propylene sulfide); poly(alkylene thiols); polyalkyleneimines such as polyethyleneimine and poly(trimethyleneimine); poly(alkylenepolyamines) such as those prepared by reacting smaller alkylenepolyamines or simple amines with either alkylene dihalides or with epichlorohydrin; poly(vinylamines); poly(allylamines); poly(aminostyrene); and like polymers containing alcohol, thiol, and amine groups.

Synthetic polymers containing more than one reactive group, such as poly[4-(1-hydroxy-3morpholinopropyl)styrene], poly[4-(1-hydroxy-3-piperidinopropyl)]styrene, poly[4-(1-hydroxy-3-dimethylaminopropyl)styrene, as well as copolymers such as hydroxyethyl acrylamide or methacrylamide with dimethylaminopropyl acrylamide or methacrylamide are also suitable for reaction with the glycoside. Proteins or protein hydrolysates, which are natural polymers containing more than one reactive group, are also suitable, e.g., the caseinates, gluten, and the like.

The reaction between the polymer and the halohydrin glycoside is a typical epoxide reaction catalyzed by base. It may be conducted by a number of techniques known in the art, for example, in an aqueous reaction medium or a polar organic solvent medium. While water is the preferred reaction medium, a homogeneous or heterogeneous system may be employed.

When an aqueous reaction medium is used, the selected polymer is dissolved or dispered in water and an aqueous solution of the glycoside reagent is then added. The reaction is carried out under alkaline conditions. The pH is about 9-13, preferably 10-12. The pH is conveniently controlled by the addition of sodium, potassium, calcium, or tetramethylammonium hydroxide. The preferred alkali is sodium hydroxyide. When the polymer contains amine groups the reaction mixture may be sufficiently basic without the addition of alkali. The reaction is carried out with stirring at a temperature of about 20°-95° C., preferably 40°-60° C. The reaction time may vary from 4-36 hours, preferably 6-24 hours, depending on such factors as the amount of glycoside reagent employed, the temperature, the pH, and the degree of substitution desired.

The polymer selected and the final derivatized product desired will determine the necessary glycoside reagent to polymer ratio employed. The amount will typically vary from about 0.1 to 100% by weight, based on the weight of the polymer. It will also depend on such factors the degree of substitution desired in the end product, and, to some extent the reaction conditions.

In an alternative method, the glycoside reagent solution is brought to the desired alkaline pH prior to its addition to the polymer solution or dispersion, this being accomplished by the addition of sufficient alkali. In another variation, the polymer solution or dispersion may be added to an alkaline solution of the glycoside reagent.

After the reaction is complete, the product is concentrated by removal of the water by vacuum distillation, after which the derivatized polymer may optionally be selectively precipitated with an organic solvent such as acetone or dialyzed to remove the unreacted residue.

The neutral derivatized polymers should find utility as thickeners. The cationic derivatized polymers can be employed as flocculants. The following test procedures were used to evaluate the derivatized polymers described herein:

CLAY FLUCCULATION TEST

A total of 38 parts Attasorb clay (obtained from Englehard Industries, Inc.) and 3462 parts water are stirred for 16 hours at room temperature. A portion of this clay suspension is added to fill a 1000 ml graduated cylinder then mixed with a plunger three times. A total of 40 ml. of a 0.1% polymer solution is then added to the clay suspension and again plunged three times. The clay flocculation time is recorded as the number of seconds necessary for the 40 ppm polymer treatment to cause the clay to flocculate and settle to the 700 ml mark of the graduated cylinder. A cationic diethylaminoethyl ether corn starch derivative useful as a clay flucculant (described in U.S. Pat. No. 2,183,093 issued on Nov. 12, 1957 to C. Caldwell et al.) which has a clay flocculation time of 70 seconds was used for comparison.

Optical Rotation

Measurement of the optical rotation is used for a qualitative indication that the reaction had occurred and for the quantitative determination of reaction efficiency. The optical rotation is measured using a Perkin-Elmer Model 14 photoelectric polarimeter. The measurement is carried out at 20° C. and the D line of a sodium lamp. It is reported as specific rotation $[\alpha]$.

The following examples will more fully illustrate the practice of this invention but they are not intended to limit its scope. In the examples, all parts and percentages are given by weight and all temperatures are in degrees Celsius unless otherwise noted.

EXAMPLE 1

This example illustrates the preparation of 3-chloro-2-hydroxypropyl glucoglycoside.

To a 0.5 liter round-bottom flask equipped with condenser, mechanical stirrer and means for heating, there was added 80 g. (0.44 mole) of dextrose, 237 g (2.15 moles) of 3-chloro-1,2-propandiol, and 20 g Dowex 50W-X8 cation exchange resin (1.9 meq/ml in H+ form. The mixture was heated to 60° C. and stirred at that temperature for 16 hours. The reaction mixture was cooled and then filtered over a gauze cloth to remove the resin. The reaction mixture was clear and light yellow in color. Unreacted diol was removed by vacuum distillation at 80° C. at 2 mm Hg. The hygroscopic solid product was slurried in acetone and filtered three times to remove residual impurities then dried in a vacuum dessicator. The light beige colored glycoside was recovered in an 80% yield (based on theoretical). $C^{13}$ NMR spectral analysis indicated the absence of the reducing carbon atom hemi-acetal signals at 92 and 96 ppm. Signals were recorded indicating a glycosidic carbon at 100.2 and 104.3 ppm corresponding to an acetal linkage. Organic chlorine analysis showed the glycoside to contain 11.5% organic chloride instead of the expected value of 13.02% based on a 272.54 molecular weight of the glycoside. This indicates that a small degree of oligosaccharide formation occurred resulting in a product containing both the glucoglycoside as well as a small amount of oligosaccharide glycoside.

EXAMPLE 2

This example illustrates the preparation of the 3-chloro-2-hydroxypropyl glycoside of a maltodextrin containing ten glucose units connected by either 1,4 or 1,6 linkages, referred to as having a D.E. of 10.

The procedure of Example 1 was followed except that the reaction time was reduced to 6 hours and the vacuum distillation step was omitted. The maltodextrin glycoside was recovered in an 84% yield (based on theoretical). The $C^{13}$ NMR spectra of the glycoside product revealed no signals corresponding to the hemi-acetal form of the reducing carbon atom of the maltodextrin. Signals were recorded at 98.6, 99.9, and 102.8 ppm corresponding to the $\alpha$- and $\beta$-glycoside carbon linkages of the maltodextrin. Analysis showed the organic chlorine content of the product to be 2.62% as compared to an expected 2.05% based on the molecular weight of the D.E. 10 glycoside. This indicates the presence of some lower molecular weight chlorohydrin glycoside present caused by slight degradation.

EXAMPLE 3

This example describes the preparation of a polyvinyl alcohol polymer with a glucose side chain. The polyvinyl alcohol used was a low molecular weight polymer sold under the tradename Gevatol 40-10 by Shawinigan Rosin Corp. It has a molecular weight of about 2,000 viscosity of 1.3–2.0 cps. 4% aqueous solution, and 75% hydrolysis of the acetyl groups. The glycoside was 3-chloro-2-hydroxypropyl glucoglycoside of Example 1. The amount of glycoside used was 20% by weight based on polyvinyl alcohol.

To a 0.25 liter round-bottom flask equipped with a condenser, mechanical stirrer, condenser, nitrogen gas inlet, and pH electrode, there was added a solution of polyvinyl alcohol (20 g.) dissolved in aqueous sodium hydroxide (0.8 g. NaOH in 30 ml. water) and then an aqueous solution of the 3-chloro-2-hydroxypropyl glucoglycoside (4 g. in 5 ml. water). The pH of the reaction mixture was maintained at 10 by adding a 10% sodium hydroxide solution as needed. The reaction mixture was held at 60° C. for 6 hours, under nitrogen, cooled to room temperature, and neutralized to pH 6.5–7.0 by adding 30% aqueous citric acid. The solution was concentrated to remove most of the water, and the product was precipitated with acetone. The precipitate was stirred with an ethanol-water mixture (85/15), centrifuged, and the supernatant was decanted off. This selective dissolution procedure was repeated three times. Acetone was then added to precipitate the product which was recovered by filtration. The product was kept in a dessicator under vacuum to remove the residual acetone.

The polyvinyl alcohol/glucoglycoside reaction product was recovered in 51.7% yield. High pressure gel permeation chromatography indicated that the product was very clean with only a fraction of polyvinyl alcohol in the product. The $C^{13}$ NMR spectra of the product showed signals between 62.3 and 77.4 ppm corresponding to the glycoside carbons. The product (1.08 g. in 100 ml. water) showed an optical rotation $[\alpha]$ of 9.73. Both 3-chloro-1,2-propanediol and polyvinyl alcohol showed no optical rotation. The 3-chloro-2-hydroxypropyl glucoglycoside starting material (1.01 g. in 100 ml. of water) had an optical rotation measured as [α] of 78.98.

EXAMPLE 4

This example illustrates reactions using a medium molecular weight polyvinyl alcohol (about 10,000 molecular weight, viscosity of 4–6 cps. as 4%, aqueous solution, and 88% hydrolysis of the acetyl groups).

Part A

The reation was carried out as in Example 3. The treatment level was 20% and the pH was maintained at 11 during the reaction. The product was isolated by precipitation in acetone and then further purified by dialysis (molecular weight cutoff of 3000). The optical rotation of the product (0.624 g. in 100 ml. of water) was measured as [α]=6.73.

Part B

The reaction was carried out as in Part A except that 50 wt.% of 3-chloro-2-hydroxypropyl glucoglycoside was used, and the reaction mixture was held for 24 hours at 60° C. The product resulting from the acetone-precipitation was pulpy and less easy to disperse in water than the starting polyvinyl alcohol. The product was purified by dialysis.

EXAMPLE 5

This example illustrates the reaction of the 3-chloro-2-hydroxypropyl glycoside of maltodetrin-10 of Example 2 with the medium molecular weight polyvinyl alcohol of Example 4. The treatment level was 40%. The reaction was carried out at pH 11.5 and 50° C. for overnight. Nitrogen gas was passed over the reaction mixture to prevent oxidation of the polyvinyl alcohol. The reaction product was dialyzed (3000 mol. wt. cut-off) and then recovered by precipitation in acetone. The product (1.04 g. in 100 ml. of water) had an optical rotation of [α]=15.32. The 3-chloro-2-hydroxypropyl maltodextrin-10 glycoside had an optical of [α]=149.5 (0.30 g. in 100 ml. water).

EXAMPLE 6

This example illustrates a reaction using a high molecular weight polyvinyl alcohol (about 90,000 molecular weight, viscosity of 28–32 cps. as 4% aqueous solution, and 99% hydrolysis of the acetyl groups).

The reaction was carried out as in Example 3. The treatment level was 40% and the pH was maintained at 10. Upon cooling and neutralization, the reaction product separated from water. It was filtered and washed with water. Since the product was not soluble in water, the optical rotation was measured in sodium hydroxide solution. The product (0.996 g. in 100 ml. of 3% NaOH) was measured as [α]=2.91. The 3-chloro-2-hydroxypropyl glucoglycoside (0.722 g. in 100 ml. of 3% NaOH solution) was measured as [α]=96.93.

EXAMPLE 7

This example describes the modification of corn gluten with the 3-chloro-2-hydroxypropyl glucoglycoside of Example 1.

The corn gluten (10 g.) was slurried in 25 ml. of water and then reacted with the above glucoglycoside at 60° C. and a pH of 11 for 6 hours. The reaction mixture was neutralized with citric acid to pH 5.6, filtered, washed, and dried.

EXAMPLE 8

This example illustrates the reaction of the 3-chloro-2-hydroxypropyl glucoglycoside of Example 1 with sodium caseinate. The reaction was carried out as in Example 7 at 40% treatment level using an excess of sodium hydroxide. The reaction mixture was maintained at 60° C. for 6 hours. Citric acid (30% aqueous solution) was added to adjust the pH to 6.5. The reaction product was dialyzed (molecular weight cut-off of 3,000), concentrated, and precipitated in acetone. The product (0.113 g. in 100 ml. of 0.1N. NaOH) showed an optical rotation of [α]= −71.34. The optical rotation of the chlorohydrin glucoglycoside was [α]=68.47 (0.119 g. in 100 ml. of 0.1N. NaOH). The optical rotation of the untreated caseinate (after dialysis) was [α]= −104.23 (0.214 g. in 100 ml. 0.1N NaOH). The reacted caseinate was less negative in optical rotation because of the glycoside pendant groups.

EXAMPLE 9

This example illustrates the reaction of the 3-chloro-2-hydroxypropyl glucoglycoside of Example 1 with a 33% aqueous solution of polyethyleneimine. The treatment level was 20%. The reaction was carried out for 6 hours at 40° C. The product was purified by dialysis. It contained no organic chlorine. The dialyzed product (0.892 g. in 100 ml. of water) showed an optical rotation of 5.04. The untreated polyethyleneimine showed no optical rotation. The starting glucoglycoside (0.736 g. in 100 ml. of water) showed an optical rotation of 73.59. The above reaction was also carried at 100% treatment.

The products were evaluated for clay flocculation using the procedure previously described. The clay flocculation times are shown below.

| Product | Flocculation Time |
| --- | --- |
| Untreated polyethyleneimine | 76 sec. |
| Polyethyleneimine treated with 20% of the chlorohydrin glucoglycoside (before dialysis) | 55 sec. |
| Polyethyleneimine treated with 20% of the chlorohydrin glucoglycoside (after dialysis) | 53 sec. |
| Polyethyleneimine treated with 100% of the chlorohydrin glucoglycoside | 46 sec. |

The polymer was more effective than untreated polymer.

EXAMPLE 10

This example illustrates the reaction of poly(dimethylaminopropyl methacrylamide) with the 3-chloro-2-hydroxypropyl glucoglycoside. The reaction was carried out with 40% treatment to alkylate some of the tertiary amino groups (25.2%). The product showed no organic chlorine. When evaluated as a clay flocculation, the treated polymer had a flocculation time of 57 sec. compared with 75 sec. for the untreated homopolymer. The improved flocculation is believed to be due to the presence of the quaternary ammonium groups.

Now that the preferred embodiments of the present invention have been described in detail, various modifications and improvements thereon will become readily apparent to those skilled in the art. Accordingly, the spirit and scope of the invention are to be limited only by the appended claims, and not by the foregoing specification.

What is claimed is:

1. A polymer represented by the formula

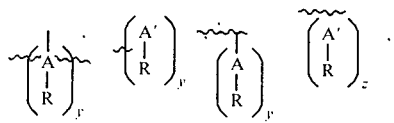

wherein A is O, S, S+ R$^1$; A' is S; R is —CH$_2$—CH(OH)—CH$_2$—O— (SAC)$_n$; R$^1$ is selected from the group consisting of R and substituted or unsubstituted alkyl, cycloalkyl, aralkyl, and alkaryl groups; (SAC)$_n$ represents a saccharide residue with n being 1-20; y and z are at least 1, with the proviso that when y and z are >1 the —(A—R)$_y$, —(A'—R)$_y$, and/or —(A'—R)$_z$ groups may be the same or different; ∼∼∼∼ represents a synthetic polymer chain; wherein the R group contains an acetal or ketal linkage from the reducing end group of (SAC)$_n$ to the 3-position of the —CH$_2$—CH(OH)—CH$_2$— and an ether or sulfide linkage from the 1-position of the —CH$_2$—CH(OH)—CH$_2$— to the O, S, S+-containing group of the polymer.

2. The polymer of claim 1, wherein A is O.

3. The polmer of claim 1, wherein A is S.

4. The polymer of claim 1, wherein y or z is >1 and A is O.

5. The polymer of claim 1, wherein y and z is >1 and A is O.

6. The polymer of claim 2, wherein

represents poly(vinyl alcohol) after the removal of a H of the alcohol group.

7. The polymer of claim 6, wherein the poly(vinyl alcohol) has a molecular weight of about 2000-90,000 and wherein (SAC)$_n$ is (glucose)$_1$ or (maltodextrin)$_{10}$.

8. A derivatized polymer prepared by reacting a synthetic polymer containing alcohol, thiol, or amine groups with a glycidyl glycoside having the formula

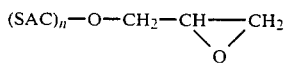

wherein (SAC)$_n$ represents a saccharide residue with n being 1-20 with the O linkage being to the reducing end of the saccharide via an acetal or ketal linkage, whereby an ether derivative, sulfide derivative, and/or amine derivative is formed.

9. The derivatized polymer of claim 8, wherein the polymer is poly(vinyl alcohol), poly(ethyleneimine), or poly(dimethylaminopropyl methacrylamide).

10. The derivatized polymer of claim 9, wherein the glycidyl glycoside is glycidyl glucoside or glycidyl maltodextrin-10.

11. A process for preparing a derivatized polymer, which comprises the steps of:
(a) dissolving or dispersing in water, a synthetic polymer containing alcohol, thiol, and/or amine groups and a 3-halo-2-hydroxypropyl glycoside having the formula

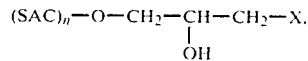

where SAC$_n$ represents a saccharide residue with n being 1-20 and X is a halogen;
(b) adjusting the pH to about 10-13 to convert the halohydrin glycoside to the glycidyl glycoside; and
(c) recovering the derivatized polymer which is the condensation reaction product of the alcohol, thiol, and/or amine group of the polymer and the glycidyl group of the glycidyl glycoside.

12. The process of claim 11, wherein the polymer is poly(vinyl alcohol), poly(ethyleneimine), or poly(dimethylaminopropyl methacrylamide).

13. The process of claim 11, wherein the 3-halo-2-hydroxypropyl glycoside is the 3-chloro-2-hydroxypropyl glycoside of glucose or maltodextrin-10.

14. The process of claim 11, wherein the polymer is poly(vinyl alcohol), poly(ethyleneimine), or poly(dimethylaminopropyl methacrylamide) and wherein the 3-halo-2-hydroxypropyl glycoside is the 3-chloro-2-hydroxypropyl glycoside of glucose or maltodextrin-10.

15. A polymer represented by the formula

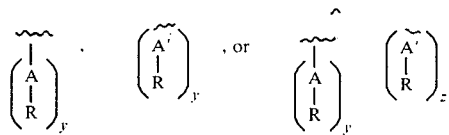

wherein A is NH, NR$^1$, N+ (R$^1$)R$^2$X$^-$; A' is N, N+HX$^-$ or N+R$^1$X$^-$; X is an anion; R is —CH$_2$—CH(OH)—CH$_2$—O—(SAC)$_n$; R$^1$ and R$^2$ are the same or different and selected from the group consisting of R and substituted or unsubstituted alkyl, cycloalkyl, aralkyl, and alkaryl groups; (SAC)$_n$ represents a saccharide residue with n being 1-20; y and z are at least 1, with the proviso that when y and z are >1 the —(A—R)$_y$, —(A'—R)$_y$ and/or —(A'—R)$_z$ groups may be the same or different; ∼∼∼∼ represents a synthetic polymer chain; wherein the R group contains an acetal or ketal linkage from the reducing end group of (SAC)$_n$ to the 3-position of the —CH$_2$—CH(OH)—CH$_2$— and an amine linkage from the 1-position of the —CH$_2$—CH(OH)—CH$_2$— to the N or N+-containing group of the polymer.

16. The polymer of claim, 15 wherein

represents poly(ethyleneimine) after the removal of the H of the imine group and wherein (SAC)$_n$ is (glucose)$_1$.

17. The polymer of claim, 15 wherein

represents poly(dimethylaminopropyl methacrylamide) after the removal of the H from the amine group and wherein (SAC)$_n$ is (glucose)$_1$.

18. The polymer of claim 15, wherein A is NH.

19. The polymer of claim 15, wherein y or z is >1.

20. The polymer of claim 15, wherein
represents poly(ethyleneimine) after the removal of the H from the imine group or poly(dimethylaminopropyl methacrylamide) after the removal of the H from the amine group.
21. The polymer of claim 20, wherein $(SAC)_n$ is $(glucose)_1$.
* * * * *

UNITED STATES PATENT AND TRADEMARK OFFICE
CERTIFICATE OF CORRECTION

PATENT NO. : 4,673,707

DATED : June 16, 1987

INVENTOR(S) : John J. Tsai, Martin M. Tessler

It is certified that error appears in the above-identified patent and that said Letters Patent are hereby corrected as shown below:

At col. 2, line 33, rewrite "wter" as --water--.

At col. 3, lines 39-41, insert commas between the alcohol groups as follows:

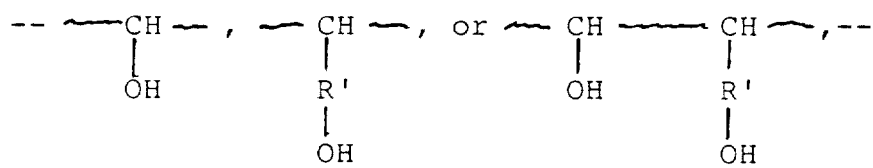

At Col. 3, lines 47-49, insert commas between the thiol groups as follows:

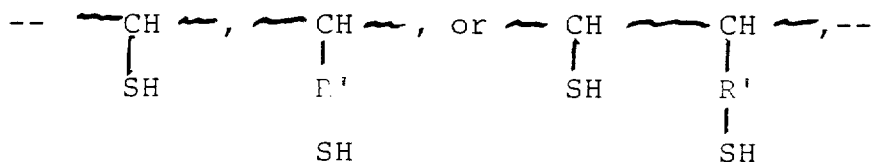

At col. 3, lines 54-60, insert commas between the amine groups as follows:

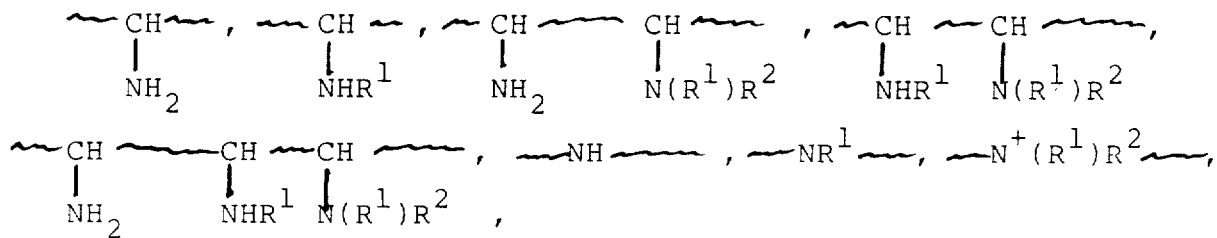

At Col. 5, line 28, rewrite "or" as --of--

UNITED STATES PATENT AND TRADEMARK OFFICE
CERTIFICATE OF CORRECTION

PATENT NO. : 4,673,707

DATED : June 16, 1987

INVENTOR(S) : John J. Tsai, Martin M. Tessler

It is certified that error appears in the above-identified patent and that said Letters Patent is hereby corrected as shown below:

At Col. 6, line 42, rewrite "dispered" as --dispersed--.

In Claim 15, at lines 29-33, correct the formula to read as follows:

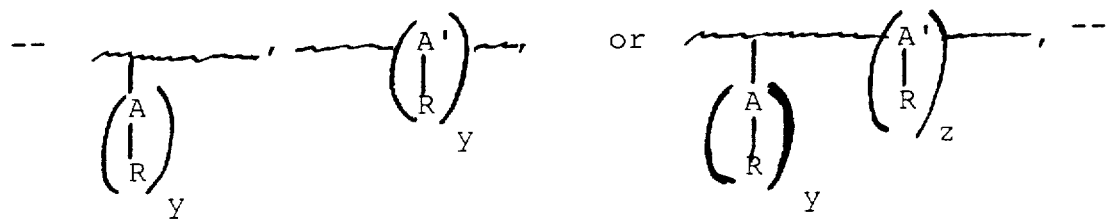

Signed and Sealed this

Thirty-first Day of May, 1988

*Attest:*

DONALD J. QUIGG

*Attesting Officer*   Commissioner of Patents and Trademarks